United States Patent [19]

Cort

[11] 4,263,283
[45] Apr. 21, 1981

[54] METHOD FOR PROPHYLAXIS AND/OR TREATMENT OF SICKLE CELL DISEASE

[75] Inventor: Joseph H. Cort, New York, N.Y.

[73] Assignee: Ferring Pharmaceuticals, Inc., New York, N.Y.

[21] Appl. No.: 150,634

[22] Filed: May 16, 1980

[51] Int. Cl.³ .................................................. A61K 37/00
[52] U.S. Cl. .................................................... 424/177
[58] Field of Search ........................................... 424/177

[56] References Cited
PUBLICATIONS

*Development of Therapeutic Agents for Sickle Cell Disease,* Inserm Symposium No. 9, Rosa et al., 1979 Elsevier/North-Holland Biomedical Press, pp. 129–137.

*Primary Examiner*—Frederick E. Waddell
*Attorney, Agent, or Firm*—Kenyon & Kenyon

[57] ABSTRACT

1-Deamino-8-D-arginine vasopressin is useful in the prophylaxis and treatment of sickle cell disease.

6 Claims, No Drawings

METHOD FOR PROPHYLAXIS AND/OR TREATMENT OF SICKLE CELL DISEASE

The present invention is concerned with a method for the prophylaxis and/or treatment of sickle cell disease.

BACKGROUND

Sickle cell disease, particularly in its homozygous form, is the result of a hereditary defect in hemoglobin biosynthesis which affects large numbers of the black population of the world and others located about the Mediterranean area. The hereditary molecular defect involves a single substitution of one valine residue for one glutamine residue in the beta chain of the hemoglobin molecule. This chemical substitution of a hydrophobic amino acid residue for a hydrophilic one makes the whole hemoglobin molecule slightly less water-soluble so that there is a tendency to crystallization of the molecule under two conditions: (1) when the pH of the extracellular body fluids decreases (i.e., acidosis with or without a high $pCO_2$), or (2) when the concentration of water in these fluids decreases (i.e., dehydration). Thus it is found that sickle cell "crises" often start at night when there is a natural tendency to dehydration and metabolic acidosis during sleep (no oral dehydration, continued formation of urine, tendency to hypoventilation, etc.).

Crystallization of the hemoglobin in the red blood cells distorts their shape into sickle-like cells, and the latter tend to have difficulty in passage through capillaries. A large concentration of sickled cells in the circulation causes aggregation of the cells in capillaries, decreases capillary flow and oxygenation of tissues, increases peripheral vascular resistance and puts a load on the heart which may result in congestive heart failure. Cases vary in frequency and severity of such "crises", the frequency varying from weekly to monthly. Severe cases have short lives, with a particularly high mortailty in young patients in many parts of the African continent. Pharmaceutical preparations so far used in an attempt to alter this sickling response of the red blood cells have in practically all instances proved as toxic or more toxic than the disease itself.

It has been known for some time that if the concentration of water surrounding sickled cells is increased either in vivo or in vitro, the sickling phenomenon can be reversed. Unfortunately, even with very large intravenous infusions of hypotonic fluids a state of sufficient hypo-osmolality is practically impossible to induce in patients, since their kidneys get rid of the water load as fast as it is given.

DESCRIPTION OF THE INVENTION

In accordance with this invention, sickle cell disease is treated by administering to a human patient an effective amount of a synthetic analog of vasopressin known as 1-deamino-8-D-arginine vasopressin, more commonly known as desmopressin or dDAVP, which is described in U.S. Pat. No. 3,497,491, and which is known to be useful as an antidiuretic.

It has been discovered in accordance with this invention that desmopressin is a safe and effective agent, when used in combination with a low salt, high water intake, for inducing a hypo-osmotic state in body fluids which, when used prophylactically, prevents red cell sickling, or when used to treat a sickling crisis, reverses sickling.

Desmopressin is uniquely suited for use in the treatment or prophylaxis of sickle cell disease. It is an active antidiuretic, which has prolonged action of from 7 to 12 hours, and which is devoid of vascular or non-vascular smooth muscle side effects at effective dosage.

The amount of desmopressin which is employed is not narrowly critical, and it is highly variable depending upon the patient. The amount can be readily determined on a case-by-case basis in accordance with known procedures to ascertain the amount of desmopressin sufficient to induce a state of hypo-osmolality sufficient to inhibit or reduce red cell sickling. As a general rule, an adequate level of hypo-osmolality is a level which is at most about 10 percent below the accepted normal value for serum osmolality (i.e., about 300 m Osm/l). That is, serum osmolality should be from about 270 to about 300 m Osm/l, and preferably from about 270 to about 275 m Osm/l. In addition, the serum sodium concentration is generally in the range of from about 120 to about 130 mM, as contrasted with a normal serum sodium concentration of about 140 mM.

Desmopressin may be administered to the patient in any convenient manner. Thus, it can be administered by injection. Alternatively, and preferably, especially where the desmopressin is to be used by the patient, it is administered intranasally, i.e., in the form of nose drops. In the latter case, however, the applied dosage of desmopressin per individual should be about ten times the dosage given by injection to achieve a comparable effect. A typical regimen for intranasal administration of desmopressin comprises administration of about 0.1 ml of a 100 $\mu$g/ml solution of desmopressin every 3 to 6 hours.

The desmopressin is administered in solution in a suitable solvent, preferably water. The solution may contain various additives generally known to the art. A preferred medium is physiological saline solution. The solution is preferably acidic, having a pH of from about 3 to about 5, and especially about 4, to stabilize the desmopressin. It is also desirable to include small amounts of bacteriostat, e.g., chlorobutanol, to minimize bacterial contamination in the intranasal preparation.

The concentration of desmopressin in the solution is not narrowly critical, and can range from about 1 $\mu$g/ml to 1000 $\mu$g/ml or higher, depending upon the intended mode of administration and dosage. In general, solutions intended for intranasal applications will contain higher concentrations of desmopressin than solutions intended to be administered by injection. Thus, solutions for intranasal administration ordinarily will contain from about 100 to about 400 $\mu$g desmopressin per milliliter, whereas injectable solutions will contain of the order of about 4 to about 10 $\mu$g desmopressin per milliliter.

The following example is illustrative.

EXAMPLE 1

The patient was a 29-year old black woman with sickle cell disease characterized by diffuse pain involving the spine, long bones and abdomen; an elevated serum bilirubin and leukocytosis (the former indicating at least temporary liver damage due to the disease); a reticulocyte count of about 15% (indicating formation of new red blood cells) and a hematocrit of 24–30% (below the normal level of 43–45%). Prior treatment included i.v. hydration, transfusion with packed red blood cells and i.v. narcotics to manage the pain.

Because of the increasing frequency and severity of sickling crises, she was treated with desmopressin to induce a state of chronic hypo-osmolality of body fluids by combination with increasd oral fluid administration.

Initially it was necessary to administer 40 mcg desmopressin (as a 100 mg/ml solution) intranasally every 6 hours to maintain a maximally concentrated urine around the clock. These maximal values, as expected in chronic sickle cell disease, initially varied from 274 to only 300 m Osm/kg. It was found that under these conditions a fluid intake of 4–5 l. daily was required to induce hyponatremia. Hydrochlorothiazide, 100 mg daily, facilitated the attainment of a hyponatremic state in this case, and the patient finally plateaued at a serum Na level of 125 [1.5 mM and urine osmolality at 344±13 m Osm/kg], fluid intake being at the level of 4.3±0.15 l/day. On this regimen and in this state she remained free of any signs of crisis for 54 days.

When the patient was removed from this regimen, her serum Na rose from 125 to 142 mM and she developed diffuse pain in long bones, ribs and shoulder and serum bilirubin rose from 1.5 to 4.0 mg%—i.e. signs of crisis. The desmopressin regimen was re-instated, her serum Na decreased again from 142 to 127 mM and pain and jaundice abated. The patient remained free of any signs or symptoms of sickle cell crisis for a period of 6 months. The hyponatremia per se has not been associated with untoward side-effects usually attributed to it, such as nausea, cramps or disturbances in central nervous function.

What is claimed is:

1. A method for the prophylaxis or treatment of sickle cell disease which comprises administering to a human patient 1-deamino-8-D-arginine vasopressin in an effective amount.

2. A method according to claim 1 comprising administering 1-deamino-8-D-arginine vasopressin to a patient undergoing a sickling crisis.

3. A method according to claim 1 comprising administering 1-deamino-8-D-arginine vasopressin prophylactically to said patient.

4. A method according to claim 1 wherein said 1-deamino-8-D-arginine vasopressin is administered intranasally.

5. A method according to claim 1 wherein said 1-deamino-8-D-arginine vasopressin is administered in an amount sufficient to reduce serum osmolality to from about 270 to about 275 m Osm/l.

6. A method according to claim 1 wherein said 1-deamino-8-D-arginine vasopressin is administered in an amount sufficient to achieve a serum sodium concentration in the range of from about 120 to about 130 mM.

* * * * *